United States Patent
Kitakawa et al.

(10) Patent No.: US 11,021,431 B2
(45) Date of Patent: Jun. 1, 2021

(54) METHOD FOR PRODUCING CINNAMIC ACID ESTER COMPOUND

(71) Applicant: TOHOKU UNIVERSITY, Sendai (JP)

(72) Inventors: Naomi Kitakawa, Miyagi (JP); Kousuke Hiromori, Miyagi (JP); Yusuke Miwa, Miyagi (JP)

(73) Assignee: TOHOKU UNIVERSITY, Sendai (JP)

( * ) Notice: Subject to any disclaimer, the term of this patent is extended or adjusted under 35 U.S.C. 154(b) by 0 days.

(21) Appl. No.: 16/622,189

(22) PCT Filed: Jun. 15, 2018

(86) PCT No.: PCT/JP2018/022904
§ 371 (c)(1),
(2) Date: Dec. 12, 2019

(87) PCT Pub. No.: WO2018/230702
PCT Pub. Date: Dec. 20, 2018

(65) Prior Publication Data
US 2020/0123094 A1   Apr. 23, 2020

(30) Foreign Application Priority Data
Jun. 15, 2017 (JP) .............................. JP2017-118111

(51) Int. Cl.
*C07C 67/08* (2006.01)
*C07C 69/732* (2006.01)
*C07C 69/734* (2006.01)

(52) U.S. Cl.
CPC ............ *C07C 67/08* (2013.01); *C07C 69/732* (2013.01); *C07C 69/734* (2013.01)

(58) Field of Classification Search
None
See application file for complete search history.

(56) References Cited

U.S. PATENT DOCUMENTS

2004/0049068 A1 * 3/2004 Palaniappan ........... C07C 67/08
560/128

FOREIGN PATENT DOCUMENTS

| CN | 104262156 A | 1/2015 |
| JP | 05-246949 A | 9/1993 |

(Continued)

OTHER PUBLICATIONS

Appendino et al. (Organic Letters, 2002, vol. 4, No. 22, 3839) (Year: 2002).*

(Continued)

*Primary Examiner* — Sudhakar Katakam
*Assistant Examiner* — Jennifer C Sawyer
(74) *Attorney, Agent, or Firm* — Sughrue Mion, PLLC

(57) ABSTRACT

A method for producing a cinnamic acid ester derivative includes reacting a cinnamic acid derivative compound represented by the formula (1), wherein the symbols are as defined in the description, with an alcohol compound represented by the formula: $R^6OH$, wherein the symbol is as defined in the description, in the presence of a strong acid resin catalyst without using a solvent. As the cinnamic acid derivative compound, cinnamic acid, ferulic acid, and caffeic acid are preferred, and as the alcohol compound, methanol, ethanol, propanol, butanol, pentanol, hexanol, ethylene glycol, glycerol, phenethyl alcohol, and a monosaccharide are preferred.

(Continued)

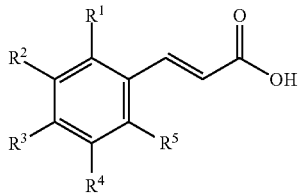

(1)

6 Claims, 1 Drawing Sheet

(56) References Cited

FOREIGN PATENT DOCUMENTS

| JP | 09-40613 A | 2/1997 |
|---|---|---|
| JP | 2003-334441 A | 11/2003 |
| JP | 2008-044859 A | 2/2008 |
| JP | 2009-089689 A | 4/2009 |

OTHER PUBLICATIONS

Riyong Huaxuepin Kexue, 2008, pp. 38-41, vol. 31, No. 12.
Hebei Daxue Xuebao et al., 1992, pp. 76-80, vol. 12, No. 1.
Shengzhao Gong, "Microwave Assist Synthesis Methyl Ferulate through a Cationic Exchange Resin Catalysis Routine," Advanced Materials Research, 2012, pp. 772-777, vols. 554-556.
Naomi Shibasaki-Kitakawa et al., "Production of high quality biodiesel from waste acid oil obtained during edible oil refining using ion-exchange resin catalysts," Fuel, 2015, pp. 11-17, vol. 139.
Rukhsana Sultana, "Ferulic acid ethyl ester as a potential therapy in neurodegenerative disorders," Biochimica et Biophysica Acta, 2012, pp. 748-752, vol. 1822.
Yean-Jang Lee et al., "Preferential cytotoxicity of caffeic acid phenethyl ester analogues on oral cancer cells," Cancer Letters, 2000, pp. 51-56, vol. 153.
Lance A. Liotta et al., "The microenvironment of the tumour—host interface," Nature, May 17, 2001, pp. 375-379, vol. 411.
Anna Rzepecka-Stojko et al., "Caffeic Acid Phenethyl Ester and Ethanol Extract of Propolis Induce the Complementary Cytotoxic Effect on Triple-Negative Breast Cancer Cell Lines," Molecules, 2015, pp. 9242-9262, vol. 20.
Shiyi Ou et al., "Seperation and purification of ferulic acid in alkaline-hydrolysate from sugarcane bagasse by activated charcoal adsorption/anion macroporous resin exchange chromatography," Journal of Food Engineering, 2007, pp. 1298-1304, vol. 78.
Feng Xu et al., "Determination of cell wall ferulic and ρ-coumaric acids in sugarcane bagasse," Analytica Chimica Acta, 2005, pp. 207-217, vol. 552.
Carmen Monente et al., "Assessment of Total (Free and Bound) Phenolic Compounds in Spent Coffee Extracts," Journal of Agricultural and Food Chemistry, 2015, pp. 4327-4334, vol. 63.
D. Grunberger et al., "Preferential cytotoxicity on tumor cells by caffeic acid phenethyl ester isolated from propolis," Experientia, 1988, pp. 230-232, vol. 44.
Aline Schar et al., "High yielding and direct enzymatic lipophilization of ferulic acid using lipase from *Rhizomucor miehei*," Journal of Molecular Catalysis B: Enzymatic, 2015, pp. 29-35, vol. 118.
Qingfang Cheng et al., "Study on novel technology for green synthesis of ethyl ferulate," China Brewing, 2009, pp. 68-69, vol. 213, No. 12.
Sheng-Zhao Gong et al., "Synthesis of methyl ferulate catalyzed by cationic exchange resin," China Surfactant Detergent & Cosmetics, Jun. 2010, pp. 186-189, vol. 40, No. 3.
International Search Report of PCT/JP2018/022904 dated Sep. 11, 2018.

\* cited by examiner

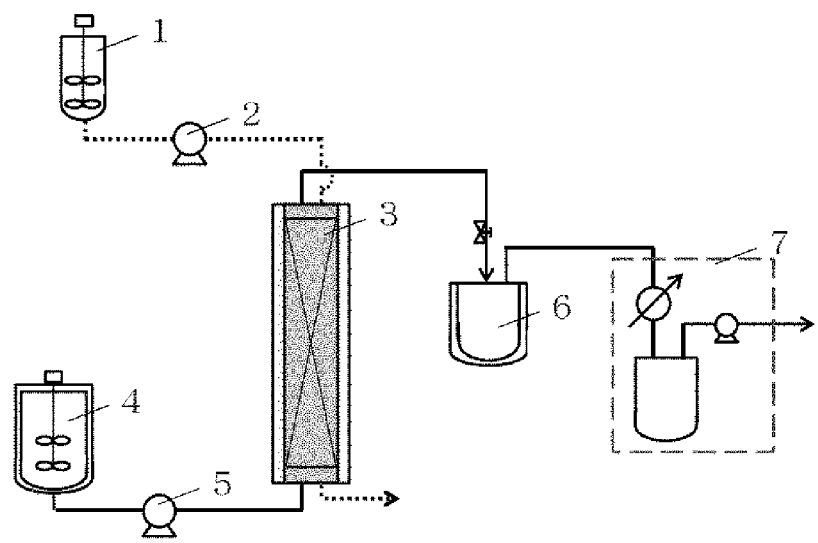

METHOD FOR PRODUCING CINNAMIC ACID ESTER COMPOUND

CROSS REFERENCE TO RELATED APPLICATIONS

This application is a National Stage of International Application No. PCT/JP2018/022904 filed Jun. 15, 2018, claiming priority based on Japanese Patent Application No. 2017-118111 filed Jun. 15, 2017.

TECHNICAL FIELD

The present invention relates to a method for producing a cinnamic acid ester compound. More particularly, it relates to a method for producing a cinnamic acid ester compound useful for medical use such as an anticancer agent or a UV absorbent from a cinnamic acid and an alcohol using an acid solid catalyst in a solvent-free system.

BACKGROUND ART

Cinnamic acids are aromatic unsaturated carboxylic acids widely present in plants. A cinnamic acid ester that is an ester form thereof with an alcohol exhibits various pharmacological activities depending on the type of the cinnamic acid or the alcohol.

For example, an ethyl ester form of ferulic acid in which $R^7$ represents a methoxy group and $R^8$ represents a hydroxy group in a chemical structure represented by the following formula (3) has a therapeutic effect on a neurodegenerative disease such as Alzheimer (NPL 1), and a methyl ester of cinnamic acid in which $R^7$ and $R^8$ each represent a hydrogen atom in the chemical structure is expected to have an effect as a UV absorbent or an antioxidant (PTL 1 and NPL 2).

[Chem. 1]

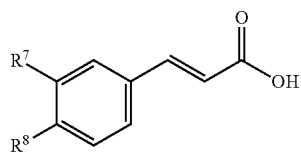

(3)

Further, caffeic acid phenethyl ester represented by the following formula (4) formed by coupling caffeic acid in which $R^7$ and $R^8$ each represent a hydroxy group to 2-phenylethanol (phenethyl alcohol) has a high anti-cancer activity and is expected to be applied to a pharmaceutical product or a food (NPL 3).

[Chem. 2]

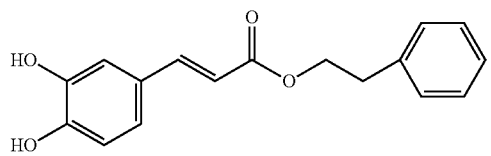

(4)

At present, as an ester form having such a pharmacological activity, one extracted from a natural product such as propolis is utilized. However, an ester content in the natural product is low (the content in an alcohol extract solution: 0.1%) and separation thereof is difficult (NPL 4), the natural product itself containing the ester is rare, and so on, and therefore, it is very expensive.

Recently, by paying attention to the fact that a cinnamic acid is contained in a degradation product of lignocellulose-based biomass at a concentration 15 to 30 times that in an extract solution, an inexpensive synthesis method using a lignin degradation product as a raw material has been proposed, and a method for synthesizing a cinnamic acid ester by esterification of a cinnamic acid in the lignin degradation product and an alcohol has been studied (NPL 5 to NPL 7).

Heretofore, as an esterification catalyst, a homogeneous phase catalyst (NPL 2 and NPL 8), a lipase enzyme (NPL 9), etc. have been studied. Grunberger et al. have reported that esterification of caffeic acid and phenethyl alcohol was performed using p-toluenesulfonic acid as a catalyst, and a yield of 40% was obtained at 60° C. for a reaction time of 96 hours (NPL 8). In addition, Lee et at. have reported that in order to increase the reaction rate or the yield, the electrophilicity of caffeic acid was enhanced by using thionyl chloride, and esterification thereof with phenethyl alcohol was performed in dioxane, and a yield of 86% was obtained at 100° C. for a reaction time of 2 hours (NPL 2). However, since a compound having high toxicity such as thionyl chloride is used, there is a problem that when a product is used in a food or a cosmetic, chromatographic separation for removing such a material is needed, and the cost burden is increased.

On the other hand, Schar et al. have reported that esterification of ferulic acid and ethanol was performed in hexane by using a lipase enzyme causing a reaction to proceed under mild conditions as a catalyst, and a yield of 76% was obtained at 61° C. for a reaction time of 72 hours (NPL 9). However, the lipase enzyme has problems that the reaction rate is slow so that a long reaction time of several days is needed, the stability of the enzyme is low so that a decrease in the activity due to the cinnamic acid itself that is a reactant or a decrease in the activity due to a solvent to be used is likely to occur, etc., and therefore, the current situation is that an enzyme having a high activity and high stability is searched for or a solvent that hardly causes a decrease in the activity of the enzyme and has high solubility of the reactant is searched for.

The present inventors have reported that a porous strongly acidic resin that is a solid catalyst expresses a high activity of fatty acid ester synthesis under a mild condition of 50° C. without a solvent, and the catalyst can be reused without decreasing the activity (NPL 10). Therefore, there is a possibility that it can also be applied to ester synthesis from a cinnamic acid and an alcohol.

Incidentally, as prior literature related to the present invention, with respect to a reaction of ferulic acid and various alcohols, in PTL 2, a method for performing the reaction in an aromatic organic solvent using a cation exchange resin catalyst is disclosed, and further, in PTL 3, a method for performing the reaction in an aqueous solvent using an esterase catalyst is disclosed.

Further, there have been a report of a reaction of ferulic acid and ethanol using various porous acidic resin catalysts (NPL 11) and a report of a reaction of ferulic acid and methanol (NPL 12). It is described that in NPL 11, a yield of 89.7% is achieved under optimal conditions (porous resin catalyst: 3.9 g, ferulic acid: 0.04 mol, ethanol: 20 mL, at a reflux temperature for 6 hours), and in NPL 12, a yield of 82.6% is obtained under optimal conditions (catalyst resin:

ferulic acid (mass ratio, the same applies hereinbelow)=12: 100, methanol:ferulic acid=7:1, at a reflux temperature for 7 hours), however, there is no report using an alcohol other than methanol and ethanol.

CITATION LIST

Patent Literature

PTL 1: JP-A-5-246949
PTL 2: JP-A-9-40613
PTL 3: JP-A-2009-89689

Non Patent Literature

NPL 1: Biochim. Biophys. Acta., 1822, 748-752 (2012)
NPL 2: Cancer Lett., 153, 51-56 (2000)
NPL 3: Nature, 411, 375-379 (2001)
NPL 4: Molecules, 20, 9242-9262 (2015)
NPL 5: J. Food Eng., 78, 1298-1304 (2007)
NPL 6: Anal. Chim. Acta, 552, 207-217 (2005)
NPL 7: Agri. Food Chem., 63, 4327-4334 (2015)
NPL 8: Experiantia, 44, 230-232 (1988)
NPL 9: J. Mol. Catal B: Enzym., 118, 29-35 (2015)
NPL 10: Fuel., 139, 11-17 (2015)
NPL 11: China Brewing., 213, 12 (2009)
NPL 12: China Surfactant Detergent & Cosmetics., 40, 3 (2010)

SUMMARY OF INVENTION

Technical Problem

Therefore, an object of the present invention is to provide a method for producing a cinnamic acid ester derivative having a useful pharmacological activity from various cinnamic acid derivative compounds and various alcohol compounds using an acidic resin as a solid catalyst that is easily separated in a solvent-free system.

Solution to Problem

The present inventors made intensive studies, and as a result, they confirmed that an ester can be synthesized in a high yield from various cinnamic acid derivative compounds and various alcohol compounds using an acidic resin that is a solid catalyst in a solvent-free system, and completed the present invention. According to the present invention, also an ester form that was required to be synthesized in multiple stages due to a large molecular weight by a known technique can be inexpensively produced in a single stage.

The present invention relates to the following method for producing a cinnamic acid ester derivative.

[1] A method for producing a cinnamic acid ester derivative, including reacting a cinnamic acid derivative compound represented by the formula (1):

[Chem. 3]

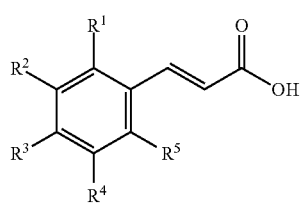

(1)

wherein $R^1$ to $R^5$ each independently represent a hydrogen atom, an alkyl group or an alkoxy group having 1 to 6 carbon atoms, or a hydroxy group, with an alcohol compound represented by the formula (2):

[Chem. 4]

$$R^6OH \qquad (2)$$

wherein $R^6$ represents an alkyl group having 1 to 12 carbon atoms or an alkylene group having 2 to 20 carbon atoms, which has at least one hydroxy group and may be branched, and the alkyl group and the alkylene group may be substituted with a phenyl group, in the presence of a strong acidic resin catalyst without using a solvent.

[2] The method for producing a cinnamic acid ester derivative according to the previous item 1, wherein the cinnamic acid derivative compound is cinnamic acid, ferulic acid, or caffeic acid.

[3] The method for producing a cinnamic acid ester derivative according to the previous item 1 or 2, wherein the alcohol compound is methanol, ethanol, propanol, butanol, pentanol, hexanol, ethylene glycol, glycerol, phenethyl alcohol, or a monosaccharide.

[4] The method for producing a cinnamic acid ester derivative according to any one of the previous items 1 to 3, wherein the cinnamic acid derivative compound is caffeic acid, and the alcohol is phenethyl alcohol.

[5] The method for producing a cinnamic acid ester derivative according to any one of the previous items 1 to 4, wherein the strongly acidic resin catalyst is a resin catalyst that is used in an alcohol-swollen state by subjecting a water-swollen type porous strongly acidic resin to a pretreatment.

[6] The method for producing a cinnamic acid ester derivative according to any one of the previous items 1 to 5, wherein a molar ratio of the cinnamic acid derivative compound to the alcohol is from 1:1 to 1:1000.

[7] The method for producing a cinnamic acid ester derivative according to any one of the previous items 1 to 6, wherein the reaction is performed in a batch system, and the strongly acidic resin catalyst is repeatedly used.

[8] The method for producing a cinnamic acid ester derivative according to any one of the previous items 1 to 6, wherein a mixture of the cinnamic acid derivative compound and the alcohol compound is passed through a column packed with the strongly acidic resin catalyst so as to continuously cause the reaction at a predetermined temperature.

Advantageous Effects of Invention

As an ester synthesis method of a known technique, the above-mentioned homogeneous phase catalyst, lipase enzyme, and the like are exemplified. However, when a homogeneous phase catalyst is used, although the reaction rate is fast, there are problems that the catalyst cannot be reused, chromatographic separation for removing the catalyst having high toxicity is needed when a product is used in a food or a cosmetic, etc. Further, when a lipase enzyme is used, although the catalyst can be reused by immobilizing the enzyme, the reaction rate is slow so that a long reaction time of several days is needed, the stability of the enzyme is low so that a decrease in the activity due to a cinnamic acid or an alcohol that is a reactant itself or a decrease in the activity due to a solvent for dissolving a cinnamic acid that is slightly soluble is likely to occur, and therefore, it is necessary to search for an enzyme having a high activity and a high stability or select a solvent that hardly causes a decrease in the activity of the enzyme and has high solubility of the reactant.

According to the present invention, by using an acidic resin that is a solid catalyst, it is possible to synthesize an ester from various cinnamic acid ester derivatives and various alcohol compounds in a solvent-free system. Further, also with respect to an ester form that was required to be synthesized in multiple stages due to a large molecular weight by a known technique, according to the method of the present invention, single stage synthesis becomes possible, and thus, inexpensive synthesis of an ester form useful for medical use or the like can be expected.

BRIEF DESCRIPTION OF DRAWING

FIG. 1 shows one example of a production apparatus (continuous flow type) for producing a cinnamic acid ester derivative of the present invention.

DESCRIPTION OF EMBODIMENTS

Hereinafter, an embodiment of the present invention will be described in detail.

A method for producing a cinnamic acid ester derivative of the present invention includes reacting a cinnamic acid derivative compound represented by the formula (1):

[Chem. 5]

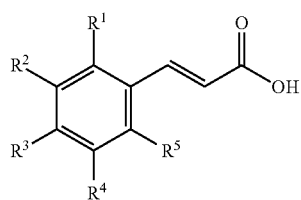
(1)

wherein $R^1$ to $R^5$ each independently represent a hydrogen atom, an alkyl group or an alkoxy group having 1 to 6 carbon atoms, or a hydroxy group, with an alcohol compound represented by the formula (2):

[Chem. 6]

$$R^6OH \qquad (2)$$

wherein $R^6$ represents an alkyl group having 1 to 12 carbon atoms or an alkylene group having 2 to 20 carbon atoms, which has at least one hydroxy group and may be branched, and the alkyl group and the alkylene group may be substituted with a phenyl group, in the presence of a strongly acidic resin catalyst without using a solvent.

In the cinnamic acid derivative compounds represented by the formula (1), cinnamic acid is a powder having a melting point of 133° C., ferulic acid is a powder having a melting point of 170° C., and caffeic acid is a powder having a melting point of 211 to 213° C., and therefore, in order to cause a reaction without using a solvent, reaction conditions for achieving a homogeneous phase state by adjusting the type of the alcohol compound to be reacted or the feeding amount thereof, or the reaction temperature are selected and applied. Incidentally, a solvent that does not inhibit the esterification reaction of the cinnamic acid derivative compound represented by the above formula (1) and the alcohol compound of the above formula (2) may be used on a timely basis. When another solvent is used other than the reaction mixture, it is necessary to remove the solvent after the esterification reaction, and from the viewpoint of productivity and cost reduction, a system that does not use another solvent is preferred.

Among the cinnamic acid derivative compounds, preferably cinnamic acid, ferulic acid, caffeic acid, p-coumaric acid, or sinapinic acid can be favorably used. Above all, cinnamic acid, ferulic acid, and caffeic acid are particularly preferred.

Further, as the alcohol compound, methanol, ethanol, propanol, butanol, pentanol, hexanol, ethylene glycol, glycerol, phenethyl alcohol, or a monosaccharide can be favorably used.

In the present invention, as a solid catalyst, a known porous strongly acidic ion exchange resin (sometimes referred to as cation exchange resin or strongly acidic ion exchange resin) is used. As the cation exchange resin, one in which a resin backbone has various chemical structures can be used as a non-soluble carrier. Specifically, for example, a synthetic polymer such as polystyrene crosslinked with divinylbenzene or the like, polyacrylic acid, a crosslinked poly(meth)acrylic acid ester, or a phenol resin, a crosslinked body of a naturally produced polysaccharide such as cellulose, etc. are exemplified. Among these, a synthetic polymer is preferred, and a crosslinked polystyrene is more preferred. The degree (level) of crosslinking depends on the used amount of divinylbenzene with respect to the total amount of a monomer, and is, for example, selected from a range of 1 to 30 mass %. At that time, as the degree of crosslinking is lower, a reactant having a large molecular size is more easily diffused inside, but the functional group concentration is decreased, and therefore, there exists an optimal value for expressing a high catalytic activity for the esterification reaction.

In the present invention, the type of the resin to be used is not particularly limited, however, for example, Diaion PK series (manufactured by Mitsubishi Chemical Corporation), Diaion SK series (the same as the above), RCP160M (the same as the above), Amberlight series (manufactured by The Dow Chemical Company), Amberlyst series (the same as the above), etc. can be exemplified. These have a copolymer backbone of styrene and divinylbenzene and contain a sulfonic acid group as an exchange group, and PK208LH, PK212LH, and PK216LH have a porous-type structure, SK104H has a gel-type structure, and RCP160M has a highly porous-type structure. The gel type is a crosslinked polymer that is uniform inside the particle. The porous type is a resin having a structure in which holes (pores) are physically formed in a gel-type resin. The highly porous type is a resin that has a high degree of crosslinking, and has a structure with a larger specific surface area or pore volume than the porous type.

As the strong acid cation exchange resin, a resin having a carboxyl group can also be applied other than a sulfonic acid group type.

The porous strongly acidic resin catalyst is in a water-swollen state, although a functional group of any resin is of $H^+$ type (≥99 mol %) showing a catalytic activity at the time of factory shipment, and therefore, it is preferred to perform, as a pretreatment, a treatment for bringing the catalyst into a state of being swollen with an alcohol that is a reactant. The pretreatment can be performed by packing a resin in a glass column (Kiriyame Glass Work Co., Tokyo, ILC-C-11) with an inner diameter of 11 mm and allowing an alcohol to pass through the column at 2.5 cm³/min until the water content of the washing liquid is decreased to less than 5 mass % according to a method (Fuel., 139, 11-17 (2015)) proposed by the present inventors.

The molar ratio of the alcohol to the cinnamic acid derivative compound may be a ratio that is larger than 1:1 and is capable of adjusting the mixture to a homogeneous phase at the reaction temperature. For example, the alcohol and the cinnamic acid derivative compound can be used at the molar ratio of the alcohol to the cinnamic acid derivative compound of 1:1 to 1:1000, preferably 1:1 to 1:200, more preferably 1:1 to 1:100 in view of the reaction ratio and the production cost.

When the alcohol which cannot adjust the mixture to a homogeneous phase at the reaction temperature is used, the cinnamic acid is deposited and cover the holes of the resin so as to restrict the contact of the reactant with a catalytic active site, resulting in a decrease in reaction efficiency. Further, the liquid cannot be made to pass therethrough in a continuous flow manner, and therefore, it is not preferred from the viewpoint of productivity.

The porous strongly acidic resin catalyst can be used by repeating the operation of an esterification synthesis reaction and a resin regeneration treatment. That is, reuse of the resin is achieved. For example, the resin after an esterification experiment is recovered by suction filtration, and the resin is packed in a column in the same manner as the pretreatment at the time of purchase, and then, the resin is washed by allowing methanol that is a reactant to pass therethrough, whereby the resin can be regenerated. In such a manner, the reactants or the product remaining inside the resin or on the surface of the resin can be removed.

[Continuous Flow-Type Esterification Reaction by Packing Porous Strongly Acidic Resin Catalyst]

In the present invention, the esterification reaction of the cinnamic acid derivative compound represented by the above formula (1) and the alcohol compound represented by the above formula (2) can be performed by allowing the reactants to flow through a continuous flow-type catalyst phase packed with the porous strongly acidic resin catalyst. An outline of an example of an apparatus for carrying out the process of the continuous flow-type esterification reaction is shown in FIG. 1. In the drawing, 1 denotes an alcohol tank, 2 denotes a pump for swelling, 3 denotes an esterification column, 4 denotes a raw material (cinnamic acid derivative compound) tank, 5 denotes a raw material supply pump, 6 denotes a product tank, and 7 denotes an alcohol removing device.

The reaction operation can be simply and promptly carried out by allowing a homogeneous mixture of the cinnamic acid derivative compound and the alcohol compound to pass through a continuous flow-type column (tower) packed with the porous strongly acidic resin catalyst at a predetermined temperature. Incidentally, in the present description, this flow type is sometimes referred to as continuous flow. The liquid passing rate of the reaction mixture through the resin bed is preferably, for example, from about 0.1 to 100 mL/min per liter of the resin. When the liquid passing rate is less than 0.1 mL/min per liter of the resin, the esterification ratio is improved, but a decrease in the productivity is caused. Further, when the liquid passing rate exceeds 100 mL/min per liter of the resin, the reaction of the reaction mixture with the catalyst is suppressed, and a decrease in the yield of the ester form after the reaction may be caused.

In the method for producing a cinnamic acid ester derivative using the continuous flow-type column (tower), the reaction mixture is brought into a homogeneous phase state to cause the reaction by adjusting the type of the alcohol compound to be reacted and the feeding amount thereof, and the reaction temperature without using another solvent other than the reaction mixture. In the present invention, a solvent that does not inhibit the esterification reaction may be used as a column mobile phase on a timely basis.

In the esterification reaction of the present invention, the contact of the reactants with the strongly acidic resin catalyst can be performed by a batch method (batch system) and a continuous flow method (flow system). Examples of the form of the apparatus include an apparatus provided with a treatment bath, and an apparatus in which the resin is transferred through a circulation system or a countercurrent system. Examples of a contact method include flowing (a method of allowing the solution to pass through the packed bed of the ion exchange resin), stirring (a method using a stirring bath), fluidization (a fluidized bed reactor), and shaking (a shaking-type reactor). It is also possible to use a liquid passing-type through a column in which an inlet port for a supply raw material and a recovery port for a product are constant, an expanded bed (an expanded bed column), a batch type, or the like.

[Batch-Type Esterification Reaction Using Various Resins]

In the present invention, the above-mentioned known porous strong acid ion exchange resin is used as a solid catalyst.

An experiment in which ferulic acid (Wako Pure Chemical Industries, Ltd., Osaka, ≥95%) was used as the cinnamic acid derivative compound, and methanol (Wako Pure Chemical Industries, Ltd., 1st grade) was used as the alcohol will be described. The present experiment without using a solvent was performed, for example, at a reaction temperature of 50° C. at which ferulic acid (powder) is dissolved in methanol to form a homogeneous phase.

An experimental apparatus (not shown) is composed of a general glass reactor, a shaker, and a thermostat bath. The reaction solution was adjusted so that the molar ratio of ferulic acid to methanol was 1:20. In the glass reactor, 20 g of the reaction solution was placed and preheated in the thermostat bath (Yamato Scientific Ltd., shaking bath, BW400, immersion constant-temperature unit, BF200) so that the reaction temperature was 50° C., and thereafter, the resin in an alcohol-swollen state preheated in the same manner was fed thereto in an amount of 33 mass % with respect to the total reaction system, followed by shaking at 150 spm (strokes per minute). Further, for comparison, an experiment using sulfuric acid as a general homogeneous phase catalyst was also performed in the same manner. The sulfuric acid concentration was made equal to that of PK208LH serving as the standard of the catalytic active group concentration and set to 2.2 mass %.

In the reaction using the above-mentioned porous strong acid ion exchange resin as the catalyst, reactants present in a bulk liquid phase are incorporated in the resin, and thereafter converted into a product. For that reason, the reactants or the product may remain in the resin. Therefore, in order to confirm the material balance, a washing operation for eluting the components contained in the resin after the reaction to the outside the resin was performed. This operation was performed by recovering 5 g of the resin after the esterification experiment by suction filtration, and thereafter adding 50 $cm^3$ of the alcohol that is a reactant thereto, followed by shaking at 150 spm for 6 hours at room temperature, so as to elute the product or the reactants remaining in the resin into the bulk liquid phase side. The operation was performed until the reactant or the product was not detected in the bulk liquid phase. In each experiment, about 0.05 g of the reaction solution was collected at predetermined time intervals and appropriately diluted with methanol, and the resulting solution was used as a sample, and then, the concentrations of the reactants and the product were measured using an HPLC system (Waters Corp., Milford, Mass., USA) provided with a UV detector.

[Experiment of Reuse of Resin]

In the present invention, the resin can be reused by repeatedly performing the operation of ester synthesis and resin regeneration. For example, the resin after the batch-type esterification experiment is recovered by suction filtration, and the resin is packed in a column in the same manner as the pretreatment, and then, the resin is washed by allowing methanol that is a reactant to pass therethrough, whereby the resin can be regenerated. In such a manner, the reactants or the product remaining inside the resin or on the surface thereof can be removed.

In each experiment, the conversion rate of esterification can be calculated using the following formula (1).

[Math. 1]

$$\text{Conversion rate (\%)} = \{(C_{FA,0} - C_{FA,t}/C_{FA,0}\} \times 100 \tag{1}$$

In the formula, $C_{FA,0}$ denotes the initial ferulic acid concentration, and $C_{FA,t}$ denotes the ferulic acid concentration at the reaction time t.

[Synthesis Experiment of Ester Having Different Pharmacological Activity]

A synthesis experiment of an ester was performed under conditions for dissolving reactants without using a solvent to form a homogeneous phase in the same manner as described above by using caffeic acid (Wako Pure Chemical Industries, Ltd., 1st grade) and cinnamic acid (Wako Pure Chemical Industries, Ltd., special grade) as the cinnamic acid derivative compounds, and using methanol and ethanol (Nihon Alcohol Hanbai Co., Ltd., Tokyo, 99%) and phenethyl alcohol (Wako Pure Chemical Industries, Ltd., special grade) as the alcohols.

EXAMPLES

Hereinafter, the present invention will be specifically described according to Reference Examples and Examples, however, the technical scope of the present invention is by no means limited to the description thereof. Note that in the following Examples, unless otherwise specified, general methods known to a person skilled in the art were followed.

Reference Example 1: Batch-Type (Batch Method) Esterification Reaction

As a resin that is a solid catalyst, PK208LH manufactured by Mitsubishi Chemical Corporation was used. In this system, conditions without using a solvent were adopted, and therefore, a homogeneous phase was formed by setting the reaction temperature to 50° C. so as to dissolve a cinnamic acid (1) and an alcohol (2). Here, ferulic acid was used as the cinnamic acid, and methanol (MeOH) was used as the alcohol (2), and these components were mixed by setting the cinnamic acid (1): the alcohol (2) to 1:20 (molar ratio). Incidentally, the resin is of $H^+$ type ($\geq 99$ mol %) showing a catalytic activity, however, it is in a swollen state with water that is a reaction by-product of esterification at the time of factory shipment, and therefore, it was swollen with the alcohol that is a reactant, and thereafter used in the experiment. The swelling was performed by packing the resin in a glass column with an inner diameter of 11 mm and allowing the alcohol (2) to pass through the column at 2.5 cm/min until the water content of the washing liquid was decreased to less than 10 mass %.

In this experiment (batch type), 20 g of the reaction solution obtained by homogeneously dissolving by preheating in advance so that the reaction temperature was 50° C. was placed in a glass reactor, and the resin in an alcohol-swollen state preheated in the same manner was fed thereto in an amount of 33 mass % with respect to the total reaction system, followed by shaking at a stirring rate of 150 spm. During the reaction, a small amount was collected from the reaction solution at predetermined time intervals and appropriately diluted with methanol, and the yield of the reaction was traced and determined using an HPLC (Waters Corp., Milford, Mass., USA) system. The yield when the reaction time was 12 hours was 100% (conversion rate: 100%).

Reference Example 2

When the reaction was traced in the same manner as in Reference Example 1 except that ethanol (EtOH) was used as the alcohol (2) and the reaction time was set to 76 hours, the yield was 100% (conversion rate: 100%).

Example 1

When the reaction was traced in the same manner as in Example 1 except that ethylene glycol that is a polyhydric alcohol was used as the alcohol (2), the cinnamic acid (1):the alcohol (2) was set to 1:30 (molar ratio), and the reaction time was set to 96 hours, the yield was 94%.

Example 2

When the reaction was traced in the same manner as in Example 1 except that ferulic acid was used as the cinnamic acid (1), 2-ethylhexanol was used as the alcohol (2), the cinnamic acid (1):the alcohol (2) was set to 1:55 (molar ratio), and the reaction time was set to 120 hours, the yield was 100% (conversion rate: 100%).

Example 3

When the reaction was traced in the same manner as in Example 1 except that caffeic acid was used as the cinnamic acid (1), the cinnamic acid (1):methanol (2) was set to 1:50 (molar ratio), and the reaction time was set to 24 hours, the yield was 100% (conversion rate: 100%).

Example 4

When the reaction was traced in the same manner as in Example 1 except that caffeic acid was used as the cinnamic acid (1), ethanol (EtOH) was used as the alcohol (2), the cinnamic acid (1):the alcohol (2) was set to 1:50 (molar ratio), and the reaction time was set to 48 hours, the yield was 100% (conversion rate: 100%).

Example 5

When the reaction was traced in the same manner as in Example 1 except that caffeic acid was used as the cinnamic acid (1), phenethyl alcohol was used as the alcohol (2), the cinnamic acid (1):the alcohol (2) was set to 1:80 (molar ratio), and the reaction time was set to 120 hours, the yield was 100% (conversion rate: 100%).

Example 6

When the reaction was traced in the same manner as in Example 1 except that cinnamic acid was used as the cinnamic acid (1), methanol was used as the alcohol (2), the cinnamic acid (1):the alcohol (2) was set to 1:10 (molar ratio), and the reaction time was set to 12 hours, the yield was 100% (conversion rate: 100%).

The results of Reference Examples 1 to 2 and Examples 1 to 6 are summarized and shown in Table 1.

TABLE 1

| Example | Cinnamic acid (1) | Alcohol (2) | With or without solvent | Yield (%) | Reaction conditions |
|---|---|---|---|---|---|
| Reference Example 1 | ferulic acid | MeOH | without | approx. 100 | (1):(2) = 1:20, 50° C., 12 hr |
| Reference Example 2 | ditto | EtOH | without | approx. 100 | (1):(2) = 1:20, 50° C., 76 hr |
| Example 1 | ditto | ethylene glycol (HOCH$_2$CH$_2$OH) | without | 94 | (1):(2) = 1:30, 50° C., 96 hr |
| Example 2 | ditto | 2-ethylhexanol | without | approx. 100 | (1):(2) = 1:55, 50° C., 120 hr |
| Example 3 | caffeic acid | MeOH | without | approx. 100 | (1):(2) = 1:50, 50° C., 24 hr |
| Example 4 | ditto | EtOH | without | approx. 100 | (1):(2) = 1:50, 50° C., 48 hr |
| Example 5 | ditto | phenethyl alcohol | without | approx. 100 | (1):(2) = 1:80, 50° C., 120 hr |
| Example 6 | cinnamic acid | MeOH | without | approx. 100 | (1):(2) = 1:10, 50° C., 12 hr |

As shown in Table 1, in any of the cases of Examples 1 to 6 in which the cinnamic acid (1) and the alcohol (2) were reacted under various reaction conditions, the conversion rate was nearly 100%, and esterification that is a reversible reaction could be allowed to completely proceed.

REFERENCE SINGS LIST

1: alcohol tank
2: pump for swelling
3: esterification column
4: raw material tank
5: raw material (cinnamic acid derivative compound) supply pump
6: product tank
7: alcohol removing device

The invention claimed is:

1. A method for producing a cinnamic acid ester derivative, comprising a step of reacting a cinnamic acid derivative compound represented by the formula (1):

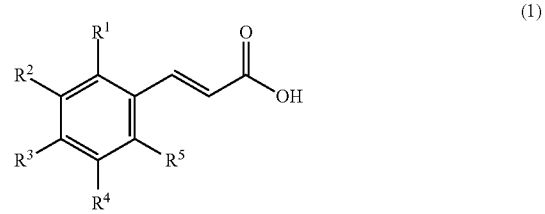

(1)

wherein $R^1$ to $R^5$ each independently represent a hydrogen atom, an alkyl group or an alkoxy group having 1 to 6 carbon atoms, or a hydroxy group, with an alcohol compound
selected from the group consisting of methanol, ethanol, propanol, butanol, pentanol, hexanol, ethylene glycol, glycerol, phenethyl alcohol, or 2-ethylhexanol, in the presence of a cation-exchange resin having copolymer backbone of polystyrene crosslinked with divinylbenzene and having a sulfonic group as an exchange group without using a solvent, provided that a reaction of a compound represented by the formula (1) where $R^2$ is a methoxy group and $R^3$ represents a hydroxy group, with methanol or ethanol is excluded.

2. The method for producing a cinnamic acid ester derivative according to claim 1, wherein the cinnamic acid derivative compound is cinnamic acid, ferulic acid, or caffeic acid.

3. The method for producing a cinnamic acid ester derivative according to claim 1, wherein the cinnamic acid derivative compound is caffeic acid, and the alcohol is phenethyl alcohol.

4. The method for producing a cinnamic acid ester derivative according to claim 1, wherein a molar ratio of the cinnamic acid derivative compound to the alcohol is from 1:1 to 1:1000.

5. The method for producing a cinnamic acid ester derivative according to claim 1, wherein the reaction step is performed in a batch system, and the cation-exchange resin is repeatedly used.

6. The method for producing a cinnamic acid ester derivative according to claim 1, wherein a mixture of the cinnamic acid derivative compound and the alcohol compound is passed through a column packed with the cation-exchange resin so as to continuously conduct the reaction step at a predetermined temperature.

* * * * *